United States Patent
Yuan et al.

(10) Patent No.: US 11,241,247 B2
(45) Date of Patent: Feb. 8, 2022

(54) SNAKELIKE SURGICAL INSTRUMENT

(71) Applicant: Shanghai Microport Medbot (Group) Co., Ltd., Shanghai (CN)

(72) Inventors: Shuai Yuan, Shanghai (CN); Youkun Jiang, Shanghai (CN); Chao He, Shanghai (CN); Yuyuan He, Shanghai (CN)

(73) Assignee: SHANGHAI MICROPORT MEDBOT (GROUP) CO., LTD., Shanghai (CN)

( * ) Notice: Subject to any disclaimer, the term of this patent is extended or adjusted under 35 U.S.C. 154(b) by 0 days.

(21) Appl. No.: 16/768,357

(22) PCT Filed: Nov. 27, 2018

(86) PCT No.: PCT/CN2018/117743
§ 371 (c)(1),
(2) Date: May 29, 2020

(87) PCT Pub. No.: WO2019/105350
PCT Pub. Date: Jun. 6, 2019

(65) Prior Publication Data
US 2020/0360038 A1    Nov. 19, 2020

(30) Foreign Application Priority Data

Dec. 1, 2017 (CN) .......................... 201711252653.9

(51) Int. Cl.
*A61B 17/29* (2006.01)
*A61B 17/00* (2006.01)

(52) U.S. Cl.
CPC ............ *A61B 17/2909* (2013.01); *A61B 2017/00438* (2013.01); *A61B 2017/00477* (2013.01);
(Continued)

(58) Field of Classification Search
CPC .............. A61B 17/00234; A61B 17/29; A61B 17/2909; A61B 17/94; A61B 2017/00305;
(Continued)

(56) References Cited

U.S. PATENT DOCUMENTS

2009/0171147 A1* 7/2009 Lee ................... A61B 17/32002
600/104
2016/0256232 A1* 9/2016 Awtar .................... A61B 34/75
(Continued)

FOREIGN PATENT DOCUMENTS

CN     194546031 A    4/2015
CN     105455902 A    4/2016
(Continued)

*Primary Examiner* — George J Ulsh
(74) *Attorney, Agent, or Firm* — Muncy, Geissler, Olds & Lowe, P.C.

(57) ABSTRACT

A snakelike surgical instrument, comprising a handheld structure (2); an manipulating structure (1) comprising an outer frame (13) hingedly connected to the handheld structure (2) so that the manipulating structure (1) has a rotational degree of freedom (R1') around a first axis and an inner frame (14) hingedly connected to the outer frame (13) so that the manipulating structure (1) has a rotational degree of freedom (R2') around a second axis, the first axis and the second axis forming an angle; an end unit (4) connected to the handheld structure (2) by means of a connecting component (3) and comprising a tool supporting base (41) and a snakelike structure (40) connected to the tool supporting base (41), the snakelike structure (40) having degrees of freedom of motion (R1, R2) in the same direction as the manipulating structure (1); and a transmission unit (5) comprising a flexible transmission structure connected to the inner frame (14) and the snakelike structure (40). A mechanical transmission mode is used by the snakelike surgical instrument, the motion of a handheld side can be directly transmitted to the end unit (4), complicated force feedback control is avoided, and control is simple.

19 Claims, 13 Drawing Sheets

(52) U.S. Cl.
CPC .............. *A61B 2017/00862* (2013.01); *A61B 2017/2903* (2013.01); *A61B 2017/2908* (2013.01); *A61B 2017/2912* (2013.01); *A61B 2017/2939* (2013.01)

(58) Field of Classification Search
CPC ........... A61B 2017/00314; A61B 2017/00318; A61B 2017/00327; A61B 2017/00477; A61B 2017/2903; A61B 2017/2908; A61B 2017/291; A61B 2017/2912; A61B 2017/2939
See application file for complete search history.

(56) References Cited

U.S. PATENT DOCUMENTS

| | | | | |
|---|---|---|---|---|
| 2019/0336230 | A1* | 11/2019 | Awtar | A61B 90/53 |
| 2021/0038865 | A1* | 2/2021 | Sharma | A61B 17/00234 |

FOREIGN PATENT DOCUMENTS

| | | | |
|---|---|---|---|
| CN | 105592801 | A | 5/2016 |
| CN | 106214257 | A | 12/2016 |
| CN | 106963494 | A | 7/2017 |
| CN | 107072684 | A | 8/2017 |
| CN | 107080588 | A | 8/2017 |
| CN | 107260307 | A | 10/2017 |
| CN | 108013906 | A | 5/2018 |
| WO | WO-2013-116869 | A1 | 8/2013 |

* cited by examiner

SNAKELIKE SURGICAL INSTRUMENT

TECHNICAL FIELD

The present disclosure relates to the field of medical instruments and, in particular, to a snake-like surgical instrument.

BACKGROUND

In minimally invasive surgery, especially laparoscopic or endoscopic surgery, due to a tiny cut, it usually requires the use of minimally invasive surgical instruments with a snake-like component which can dodge the other tissue easily during the operation in order to achieve a better treatment result with reduced damages to other tissues.

The snake-like component of the surgical instrument can imitate movements of the human hand and rotate along three orthogonal axes. For example, Chinese Published application No. CN106963494A provides a snake-like component for a surgical robot, a surgical instrument and an endoscope, in which the joint connector cooperates the flexible structure to offer the snake-like component a rotational degree of freedom.

The rotational movement of the snake-like component of the surgical instrument is usually provided by the rolling-tilt-swing mechanism of the input terminal. Chinese Published Application No. CN107072684A provides an attachment apparatus for a remote access tool, which includes a cuff configured to attach to the user's forearm and a coupling joint configured to connect the cuff to a frame so that the cuff has 1 to 4 moving degrees of freedom relative to the frame.

Chinese Published Application No. CN105592801A provides a control unit for a medical device, which includes: a palm interface engageable by a palm of a hand; a restraint capable of elastically deforming to apply a restraining force to the back of the hand; and a finger interface engageable by one or more fingers of said hand. Chinese Published Applications No. CN107080588A and No. CN107260307A provides a cable-driven minimally invasive surgery robot control device and a cable-driven minimally invasive surgery robot clamping device.

Existing surgical instruments transmit rotary movement in a electromechanical way, which generally requires a complex force feedback mechanism.

SUMMARY

Based on this, it is necessary to provide a snake-like surgical instrument with a simple control to aim at the problem of the complicated control of the snake-like surgical instrument.

A snake-like surgical instrument, including:
a hand-held component;
a connecting component;
a manipulation component comprising a hooke joint, wherein the hooke joint comprises an inner frame and an outer frame, wherein the outer frame is hinged with the hand-held component to cause the control structure to have a rotational degree of freedom about a first axis, and the inner frame is hinged with the outer frame to cause the manipulation component to have a degree of freedom of rotation about a second axis, the first axis angularly arranged with respect to the second axis;
a terminal connected to the hand-held component via the connecting component, wherein the terminal includes a jaw supporting base, a snake-like component connected to the jaw supporting base, and an end effector mounted on the snake-like component, the snake-like component having two rotational degrees of freedom; and
a transmission mechanism, wherein the transmission mechanism includes a flexible transmission structure for connecting the inner frame and the snake-like component and is configured to cause the manipulation component and the snake structure to rotate in a same direction.

The above-mentioned snake-like surgical instrument adopts the mechanical transmission and is able to directly transmit movements at the hand-held side to the terminal without a complicated force feedback control, thereby simplifying the control.

In some embodiments, the hand-held component includes an arc-shaped body. The arc-shaped body has a proximal end provided with a proximal supporting base, the proximal supporting base having a distal end connected to the manipulation component. The arc-shaped body has a distal end provided with a distal supporting base, the distal supporting base having a distal end connected to the connecting component.

In some embodiments, the first axis and the second axis are located in a centrosymmetric plane of the outer frame in a thickness direction, and are orthogonal to a center of the centrosymmetric plane.

In some embodiments, the transmission mechanism further includes a driving wheel structure mounted on the hand-held component, through which the flexible transmission structure changes direction thereof.

In some embodiments, the flexible transmission structure has one end fixed to the inner frame and the other end fixed to the snake-like component. A position at which the flexible transmission mechanism is fixed to the inner frame and a position at which the flexible transmission mechanism is fixed to the snake-like component are arranged in opposite manners.

In some embodiments, the manipulation component further comprises a gripping portion connected to the inner frame, and the gripping portion is configured to control movements of the hooke joint.

In some embodiments, the manipulation component further includes an end effector controller disposed on the gripping portion. The transmission mechanism further includes a first flexible member, through which the end effector controller controls movements of the end effector.

In some embodiments, the end effector includes at least one jaw rotatably connected to the jaw supporting base, wherein the end effector controller includes at least one opening/closing segment having one end rotatably connected to the gripping portion. The opening/closing segment controls a rotation of the at least one jaw via the first flexible member.

In some embodiments, the end effector includes two jaws that are able to rotate relative to each other, each of the two jaws rotatably connected to the jaw supporting base, and the opening/closing segment controls a relative rotation between the two jaws via the first flexible member.

In some embodiments, the end effector includes two jaws, one of the two jaws fixedly connected to the jaw supporting base, the other one of the two jaws rotatably connected to the jaw supporting base, and the opening/closing segment controls a relative rotation between the two jaws via the first flexible member.

In some embodiments, the transmission mechanism further comprises an elastic structure provided on the gripping portion, the jaw supporting base, or between the two jaws, so as to keep the two jaws open normally.

In some embodiments, the manipulation component further comprises a manipulation end connector connected to the end effector controller, and the terminal further comprises an end effector connector attached to the end effector. The end effector connector includes a first rotating shaft, a second rotating shaft and a first link rod, the first link rod having a proximal end rotatably connected to a distal end of the first flexible member via the first rotating shaft and a distal end connected to a proximal end of the jaw via the second rotating shaft. The first rotating shaft is configured to move along an axial direction of the connecting component. The manipulation end connector includes a fourth rotating shaft, a fifth rotating shaft, and a third link rod, the third link rod having a distal end rotatably connected to a proximal end of the first flexible member via the fourth rotating shaft and a proximal end rotatably connected to a distal end of the opening/closing segment. The fourth rotating shaft configured to move along the axial direction of the connecting component.

In some embodiments, manipulation component further comprises a manipulation end connector connected to the end effector controller, and the terminal further comprises an end effector connector attached to the end effector. Movements of the end effector controller are transferred to manipulation end connector that transmits the transferred movements to the end effector connector through the first flexible member, which cause the end effector connector to drive the end effector to move.

In some embodiments, the first flexible member is a soft shaft and the transmission mechanism further includes a compression spring. The compression spring is disposed between the manipulation end connector and the gripping portion, or between the gripping portion and the opening/closing segment, or in the manipulation end connector, or between the end effector and the jaw supporting base, or in the end effector.

In some embodiments, the end effector includes a left jaw and a right jaw, and the first flexible member includes a flexible elongated body. The transmission mechanism further includes a compression spring disposed between the left jaw and the right jaw.

In some embodiments, one end of the first flexible member is connected to the end effector connector and the other end of the first flexible member is connected to the manipulation end connector by passing through the gripping portion. Or, the hand-held component is provided with a driving wheel, and one end of the first flexible member is connected to the end effector connector and the other end of the first flexible member is connected to the manipulation end connector by changing an extending direction thereof via the driving wheel mounted on the hand-held component.

In some embodiments, the opening/closing segment is provided with a finger cuff.

In some embodiments, the gripping portion is rotatably connected to the inner frame to cause the gripping portion have a rotational degree of freedom about an axis of the gripping portion and cause the jaw supporting base has a rotational degree of freedom about an axis of the jaw supporting base with respect to the snake-like component. The transmission mechanism further comprises a second flexible structure, through which the gripping portion transmit rotation movements to the jaw supporting base, so as to drive the end effector to rotate around the axis of the jaw supporting base.

BRIEF DESCRIPTION OF THE DRAWINGS

In FIG. 1-FIG. 22: Manipulation component 1; Gripping portion 10; Left opening/closing segment 11; Right opening/closing segment 12; Outer frame 13; First positioning structure 131; Second positioning structure 132; Inner frame 14; Finger cuff 15; Hand-held component 2; Proximal supporting base 21; Distal supporting base 22; Connecting component 3; Terminal 4; Snake-like component 40; Jaw supporting base 41; Left jaw 42; Right jaw 43; First link rod 44; Second link rod 45; First rotating shaft 46; Second rotating shaft 47; Third rotating shaft 48; First axial limiting groove 49; Transmission mechanism 5; Flexible transmission structure 51; Flexible parts 51a, 51b, 51c, 51d; First flexible member 52; Driving wheel 53; Third link rod 71; Fourth link rod 72; Fourth rotating shaft 73; Fifth rotation shaft 74; sixth rotating shaft 75.

DETAILED DESCRIPTION

Specific embodiments of the present disclosure is described in detail with reference to the accompanying drawings to make the above objects, features and advantages of the present disclosure more apparent and readily understood. In the following description, many specific details are set forth in order to fully understand present disclosure. However, the present disclosure can be implemented in many other ways different from those described herein. Those skilled in the art can make similar modifications without departing from the spirit of the present disclosure, and the present disclosure is therefore not limited to the specific embodiments disclosed below.

The snake-like surgical instrument proposed in the present disclosure will be further described in detail below with reference to the accompanying drawings and specific embodiments. In this disclosure, in order to facilitate understanding, terms such as "proximal end" and "distal end", or "upper end" and "lower end" are used. These terms are opposing orientations, positions, and directions of elements or actions facing each other from the perspective of a doctor operating the medical instrument. The "proximal end" and "distal end", or "upper end" and "lower end" are not restrictive. Generally, the "proximal end" and "lower end" refer to an end of the medical device close to the operator during the normal operation, and the "distal end" and "upper end" refer to an end away from the operator.

Embodiment 1

Figure 1:
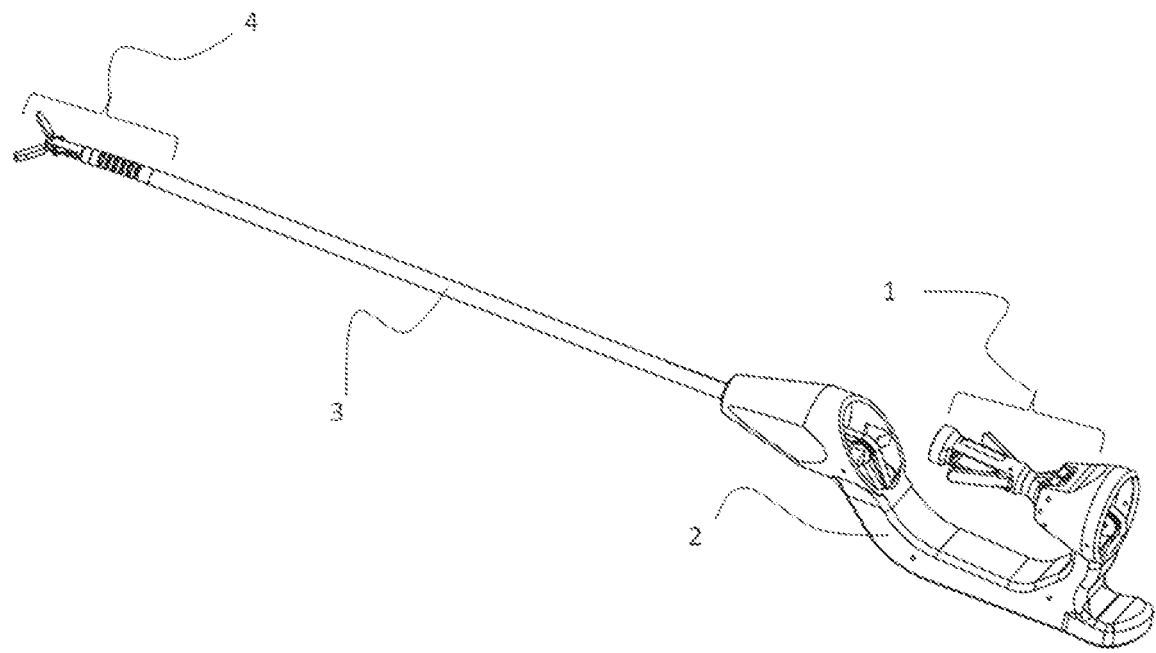
FIG. 1 is an overall schematic diagram of a snake-like surgical instrument.
Figure 10:
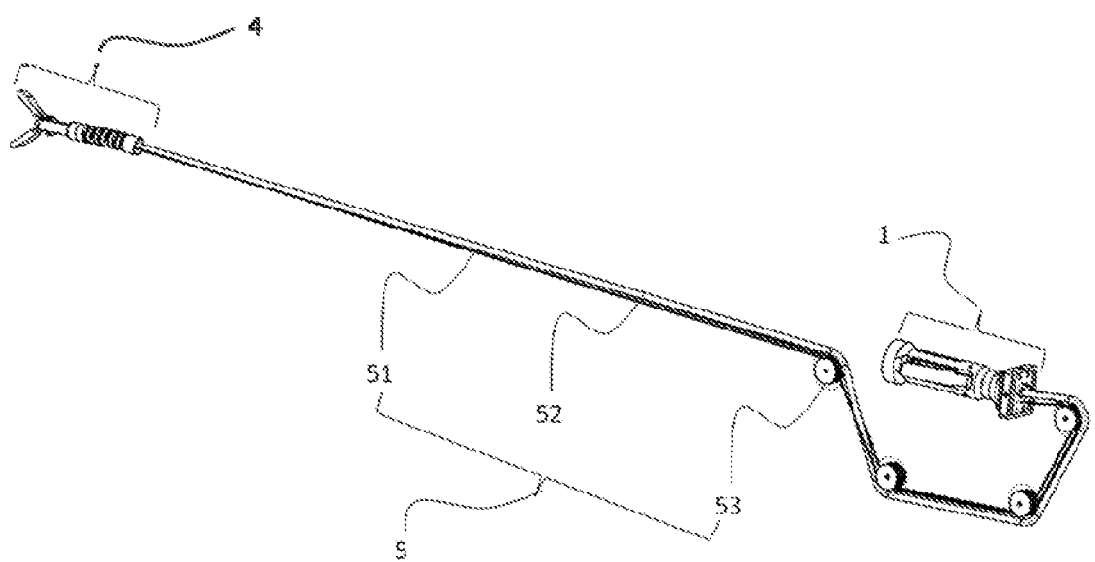
FIG. 10 is a structural schematic diagram of a transmission mechanism.

As shown in FIG. 1, the snake-like surgical instrument includes a manipulation component 1, a hand-held component 2, a connecting component 3, a terminal 4, and a transmission mechanism 5 (as shown in FIG. 10). The manipulation component 1 is disposed at the proximal end of the hand-held component 2. The proximal end of the connecting component 3 is connected to the hand-held component 2 and the distal end of the connecting component 3 is connected to the terminal 4. The manipulation structure 1 controls movements of the terminal 4 via the transmission mechanism 5. The free end of the manipulation component 1 and the free end of the terminal 4 orient a same direction. Each of the hand-held component 2 and the connecting component 3 has a passage inside. The transmission mechanism 5 may be arranged in the passage described above. However, the transmission mechanism 5 may also be positioned on outside of the hand-held component 2 and the connecting component 3.

Figure 2:
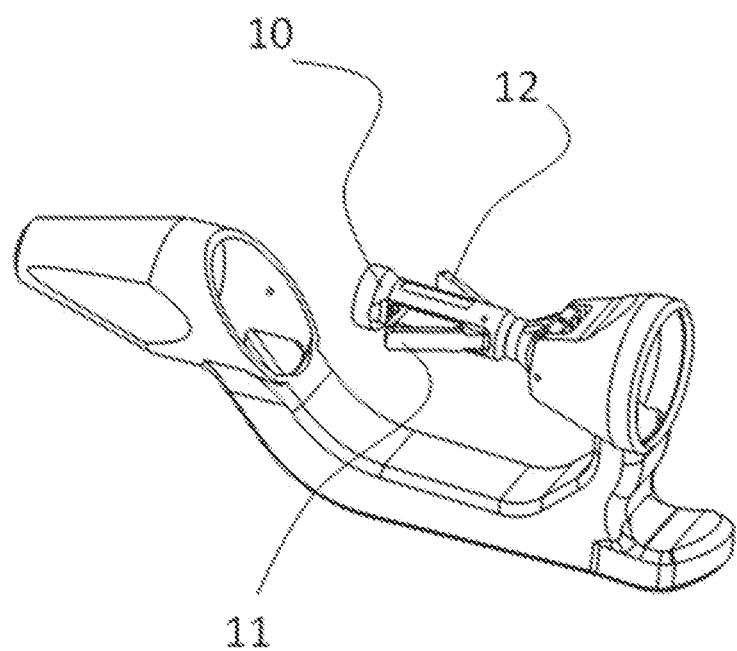
FIG. 2 is a structural schematic diagram of a manipulation component of a snake-like surgical instrument.
Figure 3:
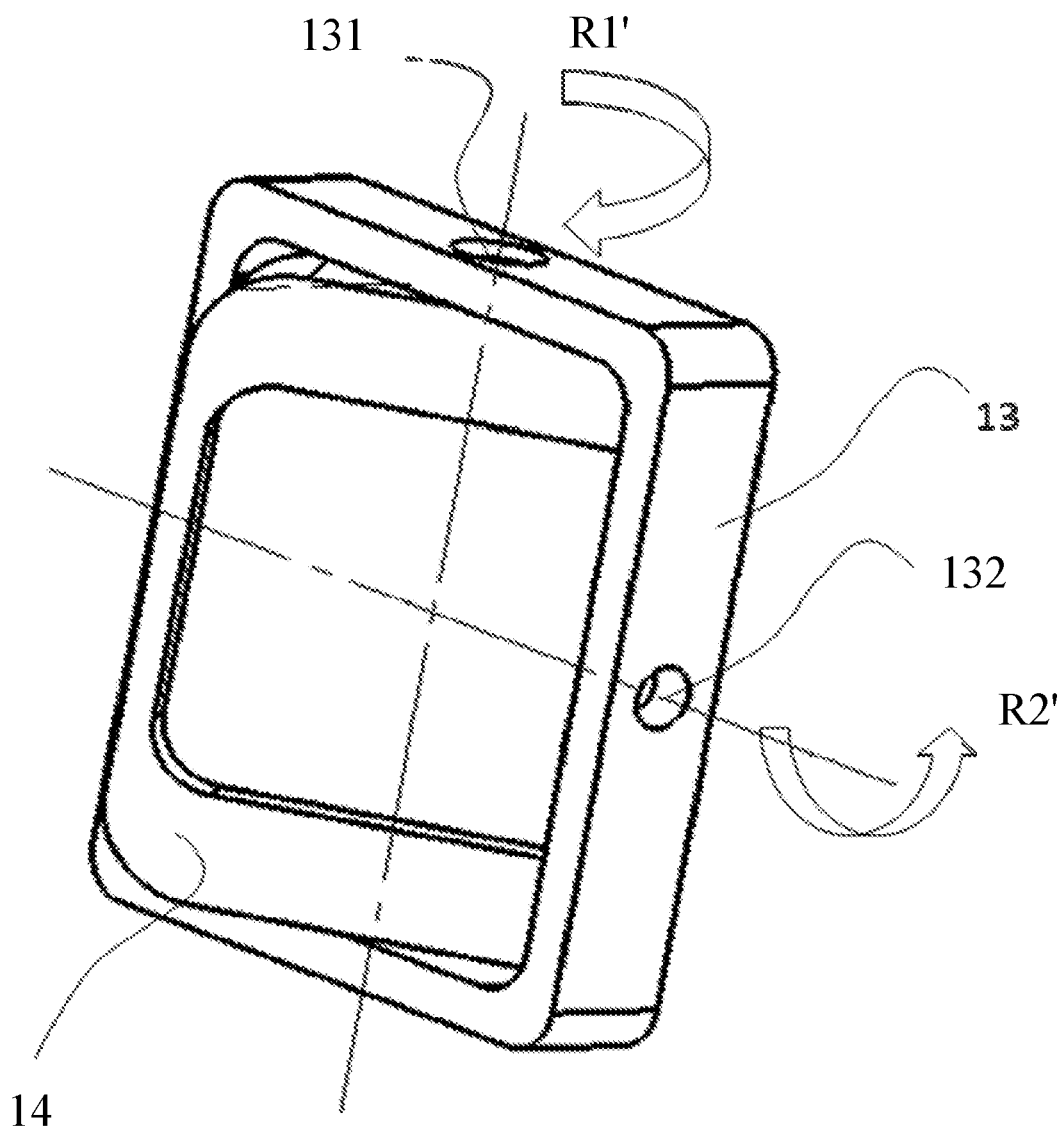
FIG. 3 is a structural schematic diagram of a hooke joint of a snake-like surgical instrument.

As shown in FIG. 2 and FIG. 3, the manipulation component 1 includes a gripping portion 10 and a hooke joint. The hooke joint includes an outer frame 13 and an inner frame 14, where the holding structure 10 is fixedly connected to the inner frame 14 of the hooke joint and the outer frame 13 of the hooke joint structure is hinged with the hand-held component 2.

Figure 4:
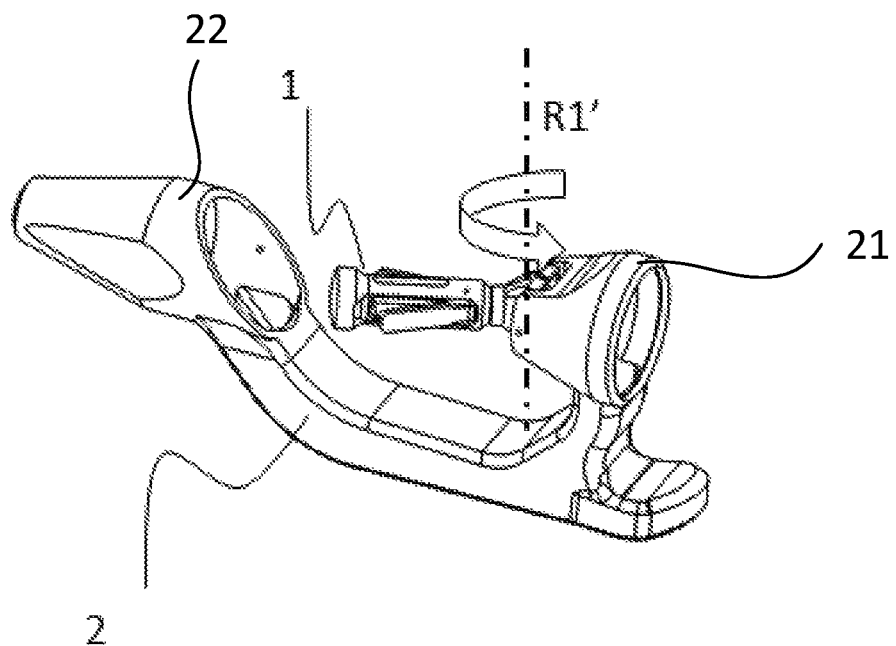
FIG. 4-FIG. 7 schematically illustrates how the snake-like surgical instrument moves at its hand-held side.

There is no particular limitation to structure of the hand-held component 2. As shown in FIG. 4, in an optional structure, the handheld structure 2 includes an arc-shaped body. The proximal end of the arc-shaped body is provided with a proximal supporting base 21, and the distal end of the arc-shaped body is provided with a distal supporting base 22. The specific curved shape of the arc-shaped body 21 is not particularly limited, and can be designed according to ergonomics. The distal end of the proximal supporting base 21 is hinged with the outer frame 13 of the hooke joint. The distal end of the distal supporting base 22 is fixedly connected to the connecting component 3.

As shown in FIG. 3, the inner frame 14 of the hooke joint is hinged to the outer frame 13 via the first positioning structure 131, and is rotatable about the first axis formed by the first positioning structure 131 to cause the manipulation component 1 to have a rotational degree of freedom R1', so that the deflection (left and right) swing of the gripping portion 10 can be achieved.

The first positioning structure 131 is preferably a positioning pin, a positioning steel ball, or the like.

The outer frame 13 has the left and right borders hinged to the distal end of the proximal support base 21 via the second positioning structure 132, and is rotatable about the second axis formed by the second positioning structure 132 to cause the manipulation component 1 have a rotational degree of freedom R2', so that the pitch (up and down) swing of the gripping portion 10 can be achieved.

The second positioning structure 132 is preferably a positioning pin, a positioning steel ball, or the like.

Further, both the first axis formed by the first positioning structure 131 and the second axis formed by the second positioning structure 132 are located in the middle plane of the hooke joint, and are orthogonal to the center point of the hooke joint, thereby improving the movement consistency between the manipulation component 1 and the terminal The middle surface of the hooke joint refers to the centrosymmetric plane of the outer frame 13 in its thickness (or height) direction, and the center point of the hooke joint refers to the center of the centrosymmetric plane. Both the first axis and the second axis are located in the centrosymmetric plane of the outer frame 13, and are orthogonal to the center of the centrosymmetric plane. In this way, the leftward swing angle of the hooke joint is in consistent with the rightward swing angle of the hooke joint, and the upward swing angle of the hooke joint is in consistent with the downward swing angle of the hooke joint, thereby improving the consistency between left and right movements of the terminal 4 and the consistency between up and down movements of the terminal 4.

Figure 5:
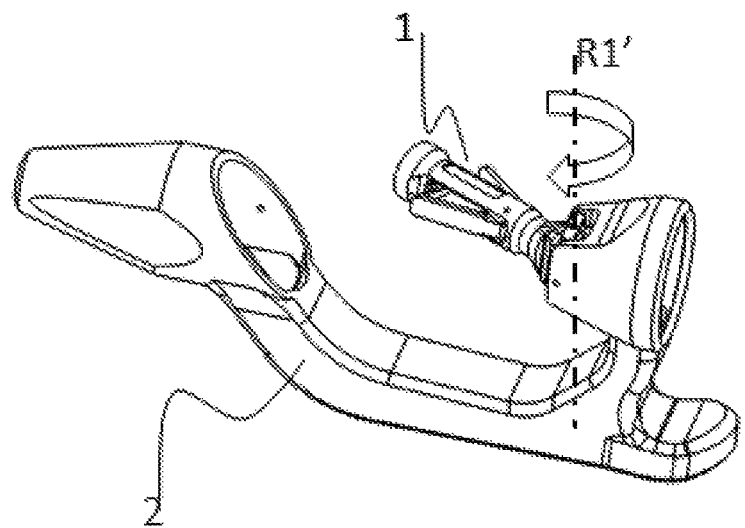
Figure 6:
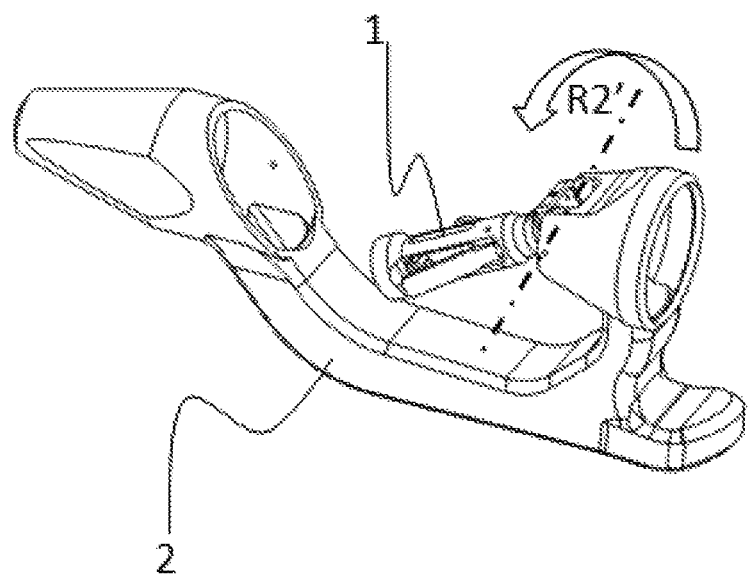
Figure 7:
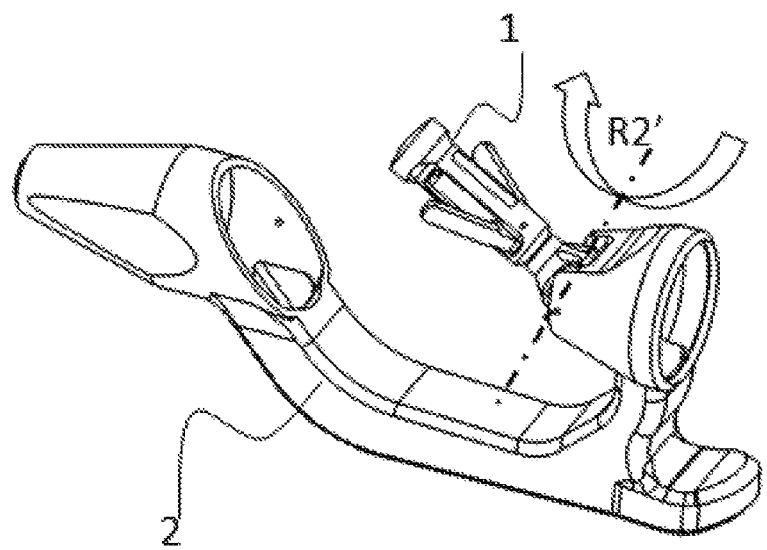

Relative movements between the manipulation component 1 and the hand-held component 2 are shown in FIGS. 4-7. FIGS. 4-5 show that the control structure 1 is able to rotate relative to the hand-held component 2 about the first axis to form a rotational degree of freedom R1'. FIGS. 6-7 show that the manipulation component 1 is able to rotate relative to the hand-held component 2 about a second axis to form a rotational degree of freedom R2'. It can be seen that, the hooke joint makes the manipulation component 1 to have two degrees of freedom relative to the hand-held component 2, in which the rotation axes of the two degrees of freedom are preferably perpendicular to each other. Of course, the two rotation axes can also be arranged in other acute angles.

Figure 8:
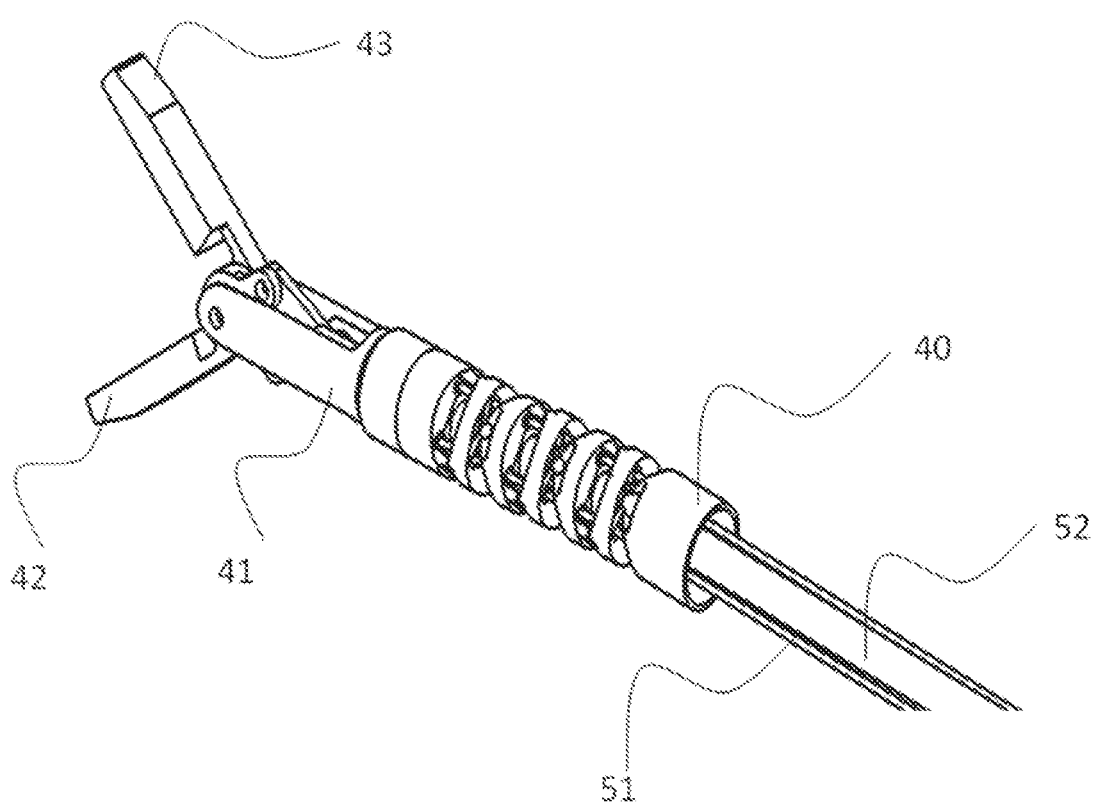
FIG. 8 is an overall schematic diagram of a terminal.
Figure 9:
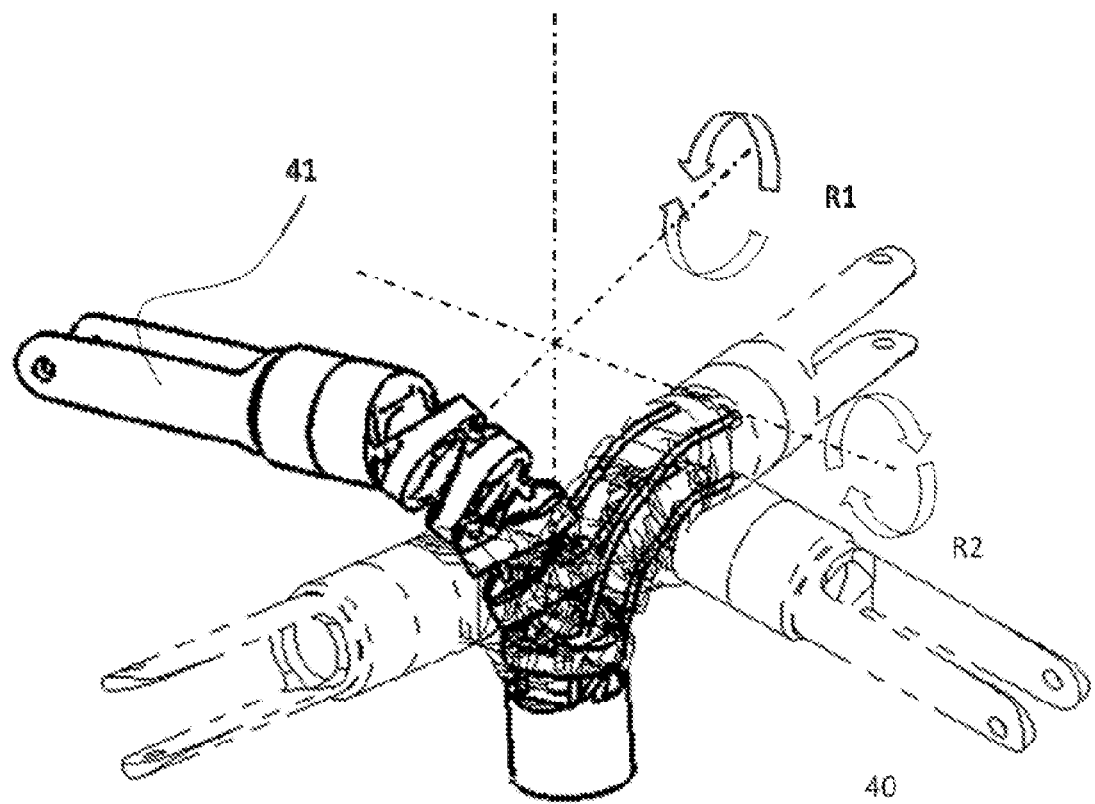
FIG. 9 schematically illustrates how the terminal moves.

As shown in FIG. 8 and FIG. 9, the terminal 4 includes a snake-like component 40, a jaw supporting base 41, and an end effector. One end of the snake-like component 40 is fixedly connected to the connecting component 3, and the other end of the snake-like component 40 is fixedly connected to the tool support base 41. The jaw supporting base 41 is used to support the end effector. The present disclosure has no particular limitation on the specific structure of the snake-like component 40, as long as it can realize swing operations about the third axis and the fourth axis (i.e., having rotational degrees of freedom R1 and R2) in two directions (preferably two perpendicular directions) that correspond to the two directions of the manipulation component 1. Similarly, the present disclosure has no particular limitation on the types of end effectors, which for example can be scissors, electric drill, clamps, and the like.

As shown in FIG. 10, the transmission mechanism 5 includes a flexible transmission structure 51, and preferably further includes a driving wheel 53. The transmission structure 51 includes a plurality of flexible transmission parts. Preferably, four flexible transmission parts are provided. One end of the flexible transmission structure 51 is fixedly connected to the inner frame 14, and the other end of the flexible transmission structure 51 is fixedly connected to the snake-like component 40 after changing its extending direction via a set of driving wheels 53 mounted on the hand-held component 2, in order to manipulate movements of the snake-like component 40. The flexible transmission structure 51 may also change its extending direction without the use of driving wheel 53.

Figure 11:
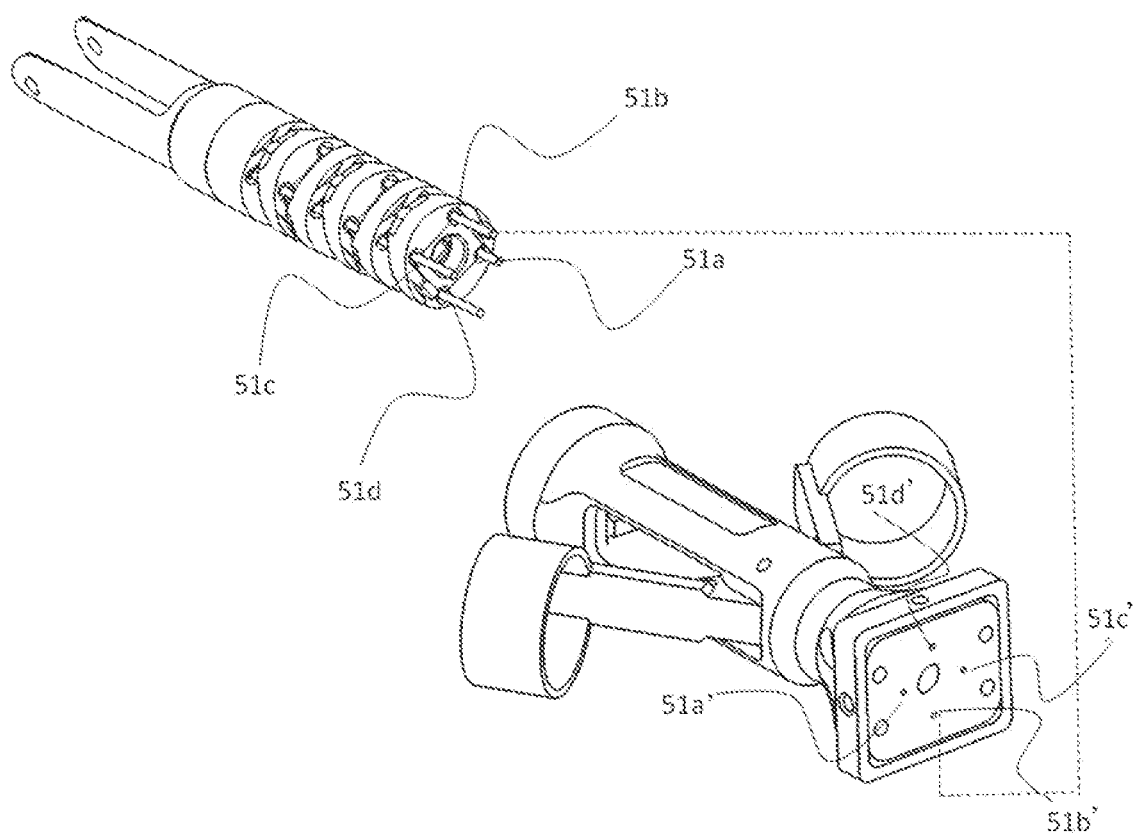
FIG. 11 schematically illustrates connections of the flexible transmission mechanism.

As shown in FIG. 11, a position at which one end of the flexible transmission structure 51 is fixed to the inner frame 14 of the hooke joint and a position at which the other end of the flexible transmission structure 51 is fixed to the snake-like component 40 are configured in an opposite manner, so that the manipulation component 1 and the terminal 4 are able to have a same movement direction when they have a same orientation direction. Here, "configured in an opposite manner" refers to being arranged in the following manner For example, when one end of the flexible transmission part is fixed to an upper side of the inner frame 14, the other end of the flexible transmission part is fixed to the lower side of the snake-like component 40; and when one end of the another flexible transmission part is fixed to the left side of the inner frame 14, the other end of the said another flexible transmission part is fixed to the right side of the snake-like component 40.

In some embodiments, as shown in FIG. 11, the flexible transmission structure 51 includes four flexible parts 51*a*, 51*b*, 51*c*, and 51*d*. In this case, the snake-like component 40 includes four connecting points, among which the upper and lower connecting points are used to control the flexible snake-like component 40 to swing up and down, and the left and right connecting points are used to control the flexible snake-like component 40 to rotate left and right. Accordingly, the inner frame 14 of the hooke joint also includes four connecting points which are connected to the four flexible parts 51*a'*, 51*b'*, 51*c'*, 51*d'* respectively from the left side in a counterclockwise manner The snake-like components 401 also includes four connecting points which are connected to the other ends of the four flexible parts 51*c*, 51*d*, 51*a*, 51*b* respectively from the left side in a counterclockwise manner. Taking 51*b* in FIG. 11 as an example, where the junction positions at both ends of 51*b* are indicated by dotted lines.

Figure 12:
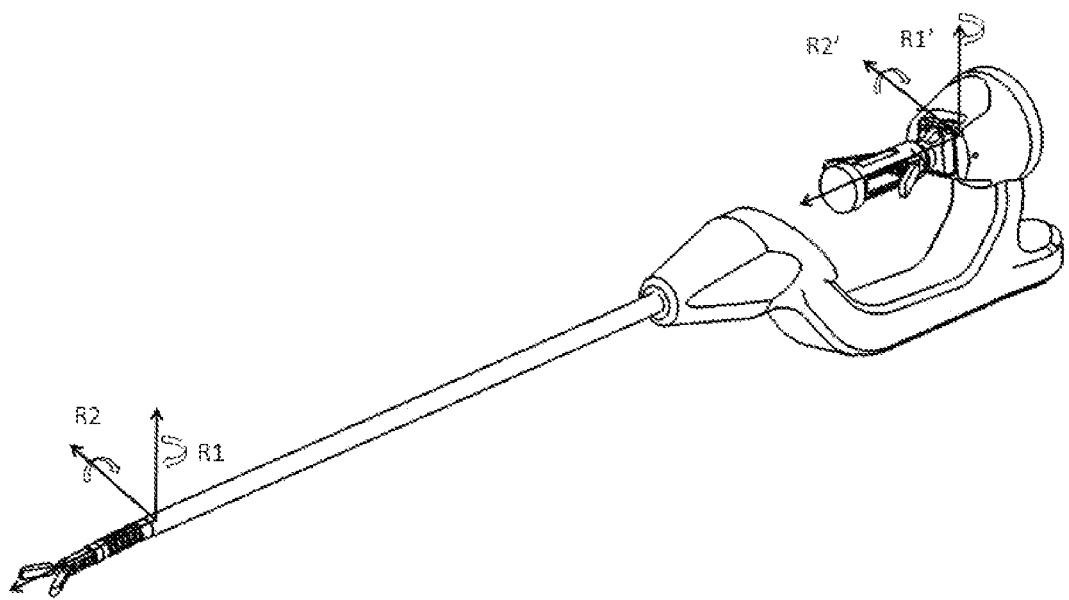
FIG. 12 schematically illustrates distributions of degrees of freedom according to embodiment 1.
Figure 13:
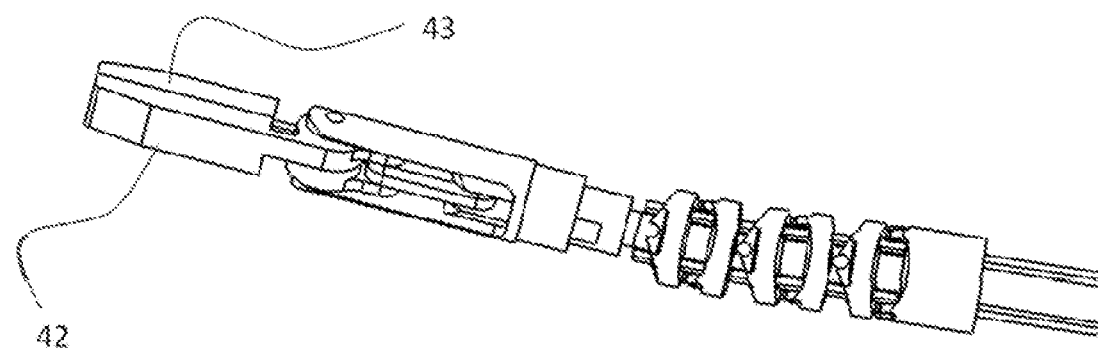
FIG. 13 and FIG. 14 schematically illustrate how to perform opening/closing movements of the end effector of the terminal according to embodiment 2.
Figure 14:
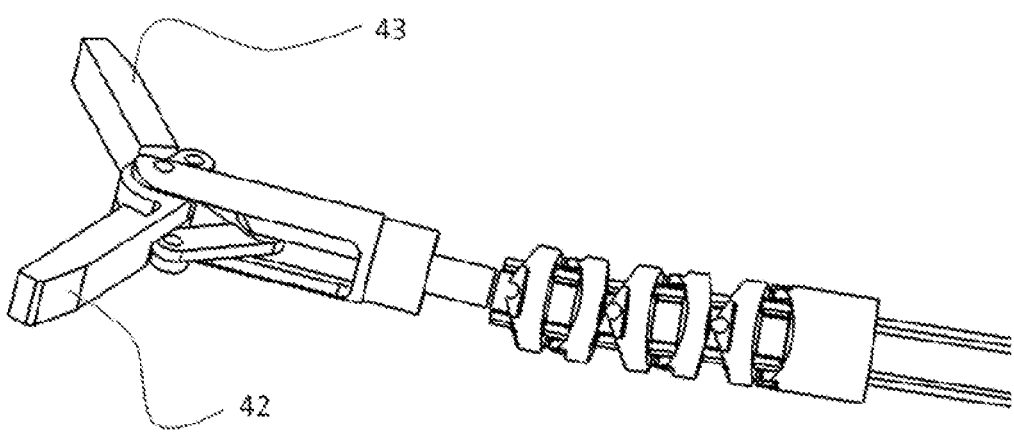
Figure 15:
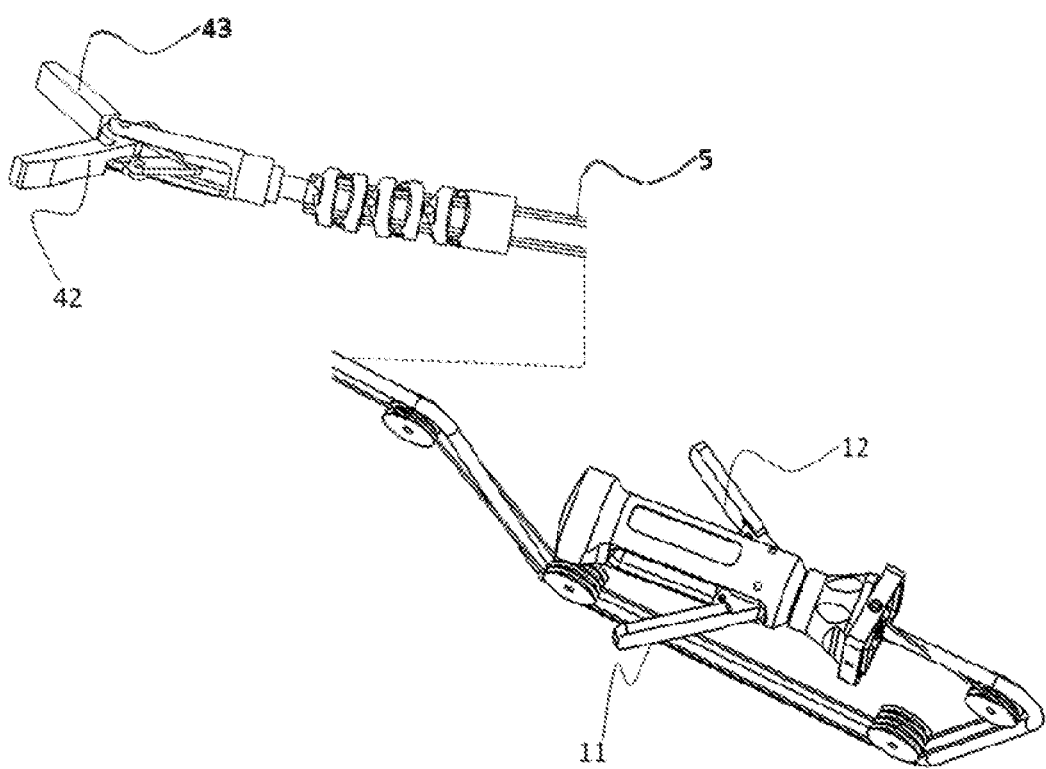
FIG. 15 and FIG. 16 schematically illustrate how the end effector of the terminal is driven to open and close according to embodiment 2.
Figure 16:
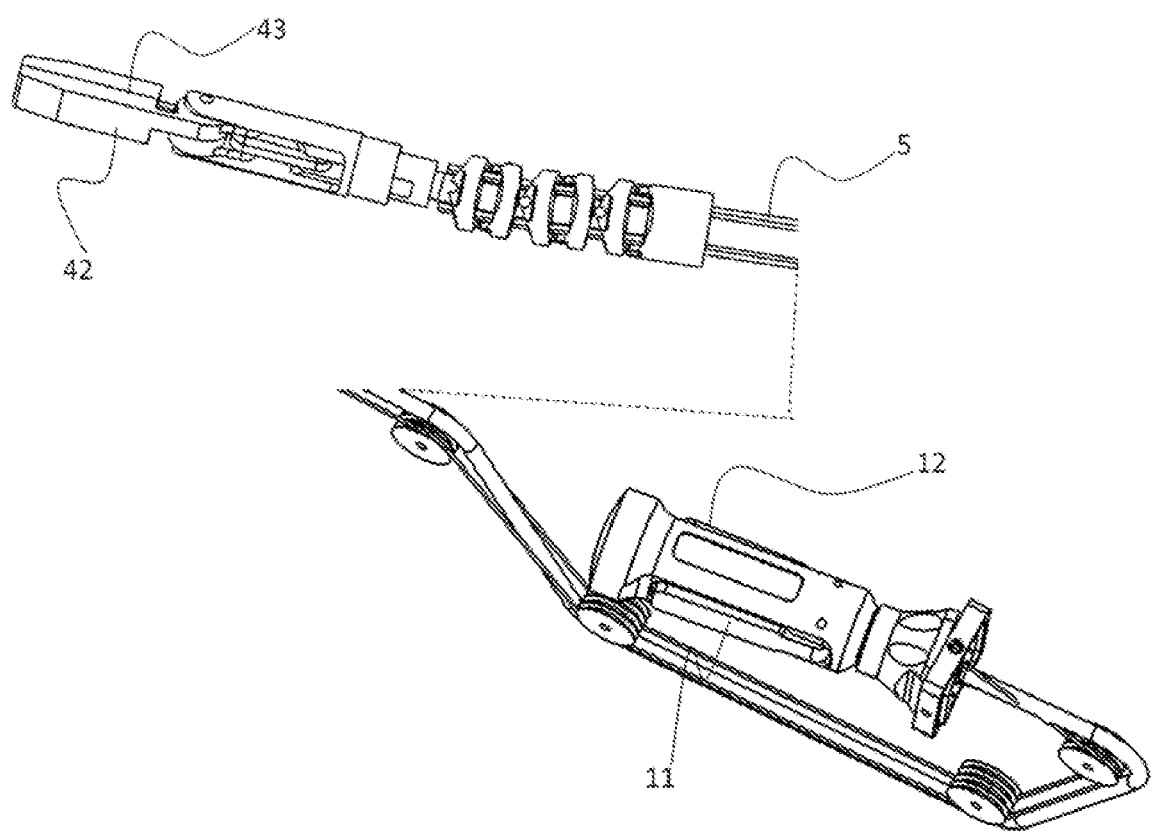

Through connections between the above components, as shown in FIG. 12, snake-like component 40 is allowed to swing about both the third and fourth axes(i.e., having rotational degrees of freedom R1 and R2) while enabling the snake-like component 40 to move, under the control of the manipulation component 1, towards the same direction as the manipulation component 1. In other words, the snake-like component 40 and the manipulation component 1 have consistent movement directions and corresponding movement amplitudes. This can prevent undesired operations of operator's forearm from being transmitted to the terminal to affect the instrument's movement accuracy. The operator can move the manipulation component 1 by manipulating the gripping portion 10 or the hooke joint. It should be appreciated by those skilled in the art that the number of attaching points on the snake-like component 40 is not limited to 4 and may be 6, 8 or the like. An increased number of such connecting points can obtain an increased control accuracy of the snake-like component 40.

Embodiment 2

The type of end effector is not limited in this embodiment. When the end effector is an instrument with a relative rotation structure, such as a scissor or a clamp, the terminal 4 of the snake-like surgical instrument is further required to have an opening/closing degrees of freedom in addition to the two rotational degrees of freedom.

For this reason, in some embodiments shown in FIG. 8, FIG. 13 to FIG. 16, the end effector has two jaws, that is, a left jaw 42 and a right jaw 43. Each of the left jaw 42 and the right jaw 43 is rotatably connected to the jaw supporting base 41. For example, the jaw supporting base 41 has a radial shaft hole. One end of the left jaw 42 is rotatably connected to the jaw supporting base 41 through the radial shaft hole, and the other end of the left jaw 42 is a free end. One end of the right jaw 43 is rotatably connected to the jaw supporting base 41 through the radial shaft hole, and the other end of the right jaw 43 is a free end. In this way, the left jaw 42 and the right jaw 43 are able to rotate about respective rotating shafts (or a same rotating shaft) to achieve relative rotation, so as to realize the opening/closing movements of the end effector, such as grasp operation.

Accordingly, the manipulation component 1 further includes an end effector controller configured to control the opening/closing movements of the end effector.

In some embodiments, the end effector controller includes a left opening/closing segment 11 and a right opening/closing segment 12, where the left opening/closing flap 11 and the right opening/closing flap 12 are disposed on the gripping portion 10 for controlling movements of the end effector of surgical instruments. Specifically, one end of the left opening/closing segment 11 is rotatably connected to the gripping portion 10, and the other end (i.e., the free end) is away from the gripping portion 10. One end of the right opening/closing segment 12 is rotatably connected to the gripping portion 10, and the other end (i.e., the free end) is away from the gripping portion 10.

Further, the left opening/closing segment 11 and the right opening/closing segment 12 are symmetrically arranged on both sides of the gripping portion 10.

Further, the manipulation component 1 further includes an opening/closing segment locking device that allows the locking function of the opening/closing segment. The opening/closing segment locking device may be a limiting mechanism mounted on the gripping portion 10, such as a locking member with a clip-on function, to lock the opening/closing segment. The locking member may only lock the opening/closing segment in a fixed open position, such as the maximum opening/closing position of the opening/closing segment. The locking member may also be a locking device capable of adjusting locking positions. When the opening/closing segment is opened to a desired position, the locking position of the locking device is adjusted to keep the opening/closing segment in the said open position.

Figure 17:
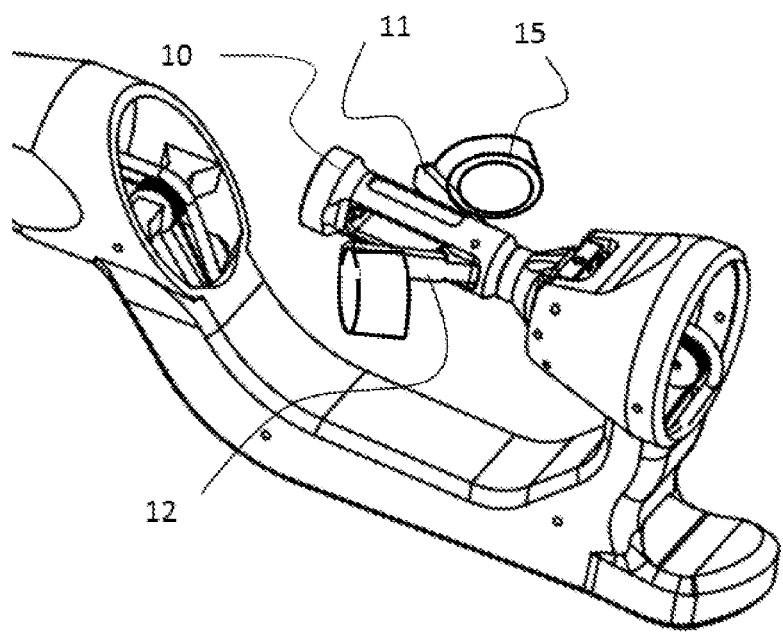
FIG. 17 is a schematic structural diagram of a manipulation component with a finger cuff.

Further, as shown in FIG. 17, each of the left opening/closing segment 11 and the right opening/closing segment 12 may be provided with a finger cuff 15 for a human finger to be placed in, allowing a more efficient control of the opening/closing movements of the opening/closing segment.

In another alternative embodiments, the end effector control includes only the left opening/closing segment 11 to control movements of the end effector of the surgical instrument. Correspondingly, one end of the left opening/closing segment 11 is rotatably connected to the gripping portion 10, and the other free end of the left opening/closing segment 11 is away from the gripping portion 10.

As shown in FIG. 10, the transmission mechanism 5 further includes a first flexible member 52. The opening/closing segment controls the opening/closing movements of the jaw through the first flexible member 52.

In some embodiments, the terminal 4 further includes an end effector connector, and the manipulation component 1 further includes a manipulation end connector. Movements of the end effector controller on the manipulation component 1 is transmitted to the manipulation end connector and then is transmitted to the end effector connector through the first flexible member 52, which cause the end effector connector to drive the jaw to move.

Specifically, the distal end of the first flexible member 52 is connected to the end effector connector, and the proximal end of the first flexible member 52 is connected to the manipulation end connector. One end of the end effector connector is connected to the first flexible member 52 and the other end of the end effector connector is connected to the end effector, so as to convert axial movements of the first flexible member 52 to opening/closing movements of the end effector.

Figure 19:
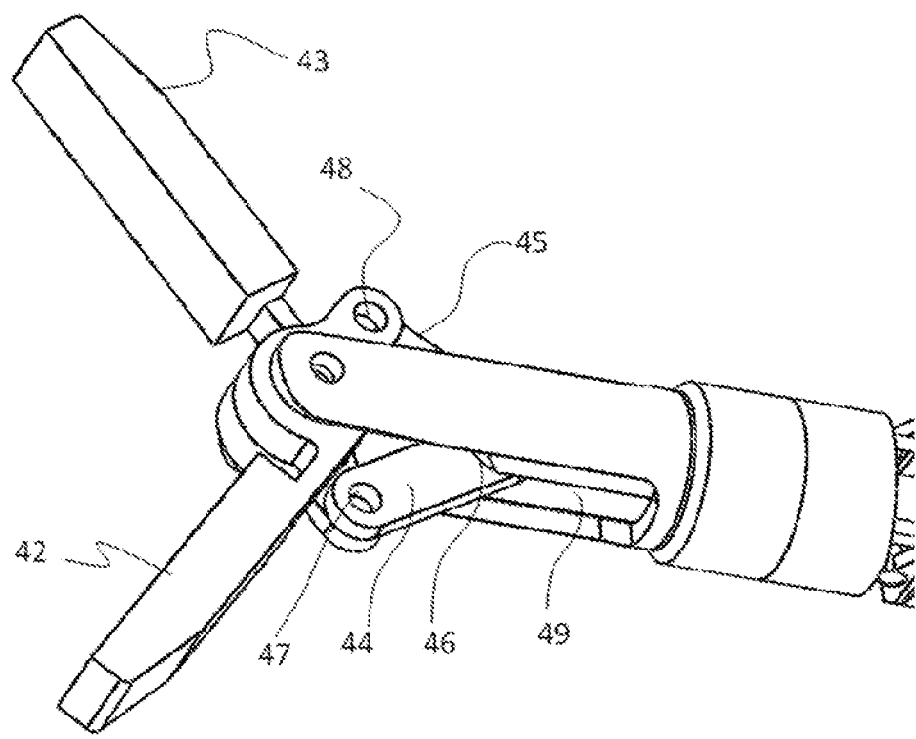
FIG. 19 is a structural schematic diagram of an end effector connector.

In some embodiments, referring to FIG. 19, the end effector connector includes a first link rod 44 and a second link rod 45, where the proximal end of the first link rod 44 is connected with the proximal end of the second link rod 45 through a first rotating shaft 46, the distal end of the first link rod 44 connected to the proximal end of the left jaw 42 through a second rotating shaft 47, the distal end of the second link rod 45 connected to the proximal end of the right jaw 43 through a third rotating shaft 48 is connected. Moreover, the first rotating shaft 46 is connected to the first flexible member 52. Under the driving of the first flexible member 52, the first rotating shaft 46 moves axially in the first axial limiting groove 49 provided on the jaw supporting base 41, which in turn makes the left jaw 42 and the right jaw 43 open and close.

On the other hand, similar to the end effector connector, one end of the manipulation end connector is connected to the first flexible member 52 and the other end of the manipulation end connector to the end effector controller (e.g., left opening/closing segment 11 and right opening/closing segment 12), so as to convert movements of the end effector controller to axial movements of the first flexible member 52.

Figure 20:
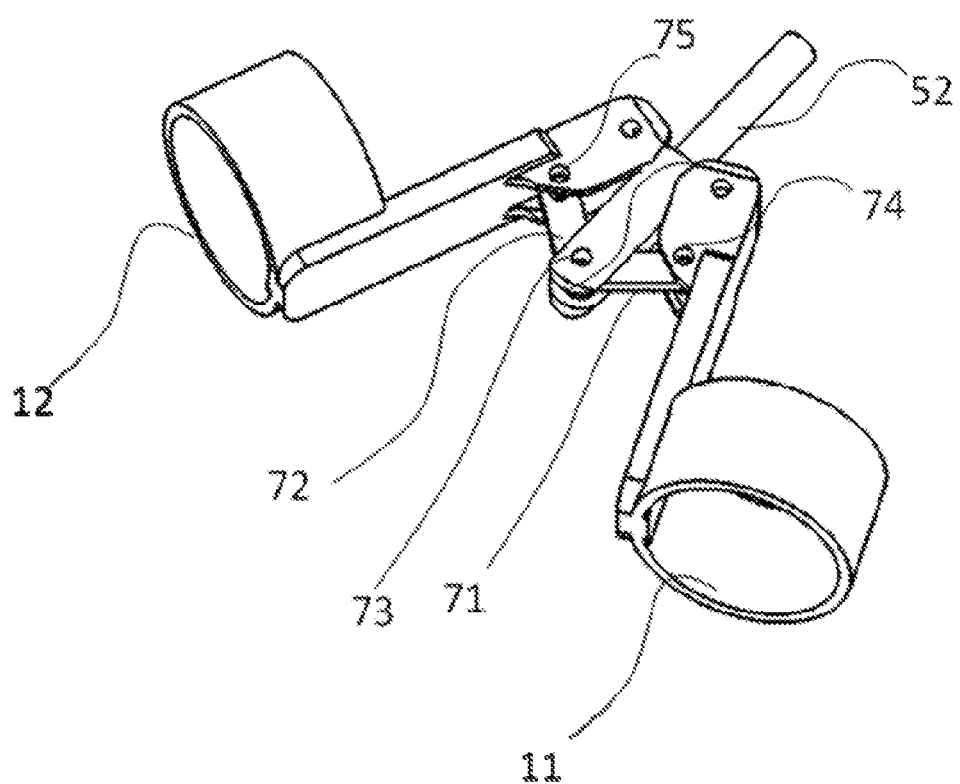
FIG. 20 is a structural schematic diagram of a manipulation end connector.

In some embodiments, referring to FIG. 20, the manipulation end connector includes a third link rod 71 and a fourth link rod 72, where the distal ends of the third link rod 71 is connected with the distal ends of the fourth link 72 through a fourth rotating shaft 73, the left opening/closing segment 11 connected to the proximal end of the third link rod 71 through a fifth rotating shaft 74, the right opening/closing segment 12 connected to the proximal end of the fourth link rod 72 through a sixth rotating shaft 75. The fourth rotating shaft 73 is connected to the first flexible member 52 and is limited by a second axial limiting groove (not labeled) disposed on the gripping portion 10. When the left opening/closing segment 11 and the right opening/closing segment 12 are driven, the fourth rotating shaft 71 axially moves relative to the gripping portion 10, which in turn drives the first flexible member 52 to move axially. The driving wheel 53 provides support if the first flexible member 52 needs to change its direction in passing through the hand-held component 2 and the connecting component 3. In this way, during the moving process, the first flexible member 52 makes movements of the opening/closing segments in consistent with movements of the jaws. That is, if the opening/closing segments open, the jaws open; and if the opening/closing segments close, the jaws close.

Further, the transmission mechanism 5 further includes an elastic structure. The elastic structure is provided on the gripping portion 10 or on the jaw supporting base 41 or between the jaws, so as to keep the two jaws normally open. This is further described below in conjunction with the embodiments.

In some embodiments, the first flexible member 52 is a soft shaft. Correspondingly, the distal end of the soft shaft is connected to the end effector connector, and the proximal end of the soft shaft is connected to the manipulation end connector to achieve opening and closing of the end effector. The elastic structure is disposed between the manipulation end connector and the gripping portion 10, or between the left and right opening/closing segment and the gripping portion 10 or in the manipulation end connector, so as to keep the end effector controller normally open; and/or, the elastic structure is disposed between the end effector and the jaw supporting base 41, or in the end effector, so as to keep the end effector controller normally open (i.e., keeping the manipulation end connector normally open).

In some embodiments, a compression spring is provided between the left and right opening/closing segments 11 and 12 and the gripping portion 10 to keep each of the free end of the left opening/closing segment 11 and free end of the right opening/closing segment 12 away from the gripping portion 10. When the jaws are needed to close, the left opening/closing segment 11 and right opening/closing segment 12 overcome resistance force from the compression spring, and rotate to move close to the gripping portion 10, so as to drive the proximal end of the first flexible member 52 to move towards the proximal end of the surgical instrument, which in turn drives the left jaw 42 and right jaw 43 to move close to each other. Upon removal of the exogenic action, the left opening/closing segment 11 and right opening/closing segment 12 rotate to move away from gripping portion 10 under the action of the compression spring, so as to drive the first flexible member 52 to move towards the distal end of the surgical instrument, which in turn drives the left jaw 42 and right jaw 43 to move away from each other.

In some embodiments, the compression spring is provided between the end effector connector and the jaw supporting base. When the jaws are needed to close, the left opening/closing segment 11 and right opening/closing segment 12 overcome resistance force from the compression spring, and rotate to move close to the gripping portion 10, so as to drive the first flexible member 52 to move towards the proximal end of the surgical instrument, which in turn drives the left jaw 42 and right jaw 43 to move close to each other. Upon removal of the exogenic action, the left jaw 42 and right jaw 43 rotate to move away from each other under the action of the compression spring, so as to drive the first flexible member 52 to move towards the distal end of the surgical instrument, which in turn drives respective free ends of the left opening/closing segment 11 and right opening/closing segment 12 to rotate away from the gripping portion 10.

In another embodiments, the first flexible member 52 includes a flexible elongated element such as a nickel titanium wire or steel wire. Correspondingly, the compression spring is provided between the end effector connector and the jaw supporting base 41. When the jaws are needed to close, the left opening/closing segment 11 and right opening/closing segment 12 overcome resistance force from the compression spring, and rotate to move close to the gripping portion 10, so as to drive the first flexible member 52 to move towards the proximal end of the surgical instrument, which in turn drives the left jaw 42 and right jaw 43 to move close to each other. Upon removal of the exogenic action, the left jaw 42 and right jaw 43 rotate to move away from each other under the action of the compression spring, so as to drive the first flexible member 52 to move towards the distal end of the surgical instrument, which in turn drives respective free ends of the left opening/closing segment 11 and right opening/closing segment 12 to rotate away from the gripping portion 10.

Figure 18:
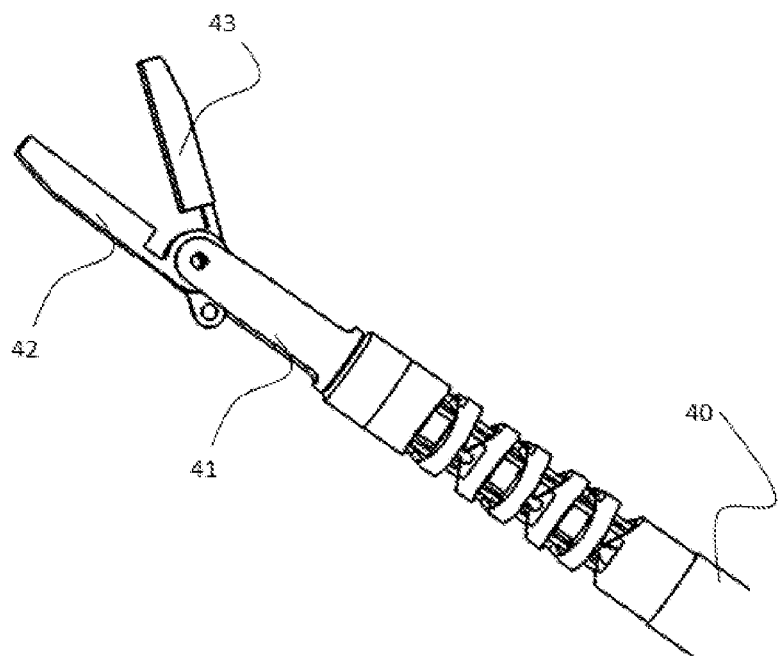
FIG. 18 is a structural schematic diagram of jaws of the terminal according to another embodiment.

In another embodiments shown in FIG. 18, the jaws include a left jaw 42 and a right jaw 43, but one of the jaws has a fixed structure. That is, only one of the left jaw 42 and the right jaw 43 is able to rotate about the radial shaft hole on the jaw supporting base 41, one of the two jaws being fixed and the other of the two jaws being rotatable, thereby forming the opening/closing movements. Correspondingly, the end effector connector has only one link rod that is rotatably connected with the rotatable jaw and has other parts similar to the end effector connector in above embodiments. In some embodiments, the opening/closing segments in the manipulation component 1 can also be correspondingly configured as: one is kept closed and immovable with the other one being operable; two opening/closing segments is operable with only one of the two opening/closing segments having its rotating shaft driven the flexible member 52 to provide driving force; two opening/closing segments is operable with each of the two opening/closing segments having its rotating shaft driven the flexible member 52 to provide driving force. In the case that one jaw has a fixed structure, the elastic member such as the compression spring can also be provided to keep the two jaws normally open.

Further, the first flexible member 52 may also be arranged such that the distal end of the first flexible member 52 is connected to the end effector connector and the proximal end of the first flexible member 52 connected to the manipulation end connector by directly passing through the distal end of the gripping portion 10 of the manipulation component 1 without having to pass through the hand-held component 2. This connection avoids changes of direction of the first flexible member 52.

The snake-like surgical instruments in the first and second embodiments further include a movement locking mechanism, so that swing movements of the snake-like component 40 in two directions are able to be locked. The locking may be achieved by locking the flexible transmission structure 51, the swing movements of the manipulation component 1 in two directions, or the swing movements of the terminal 4 in two directions.

Embodiment 3

Figure 21:
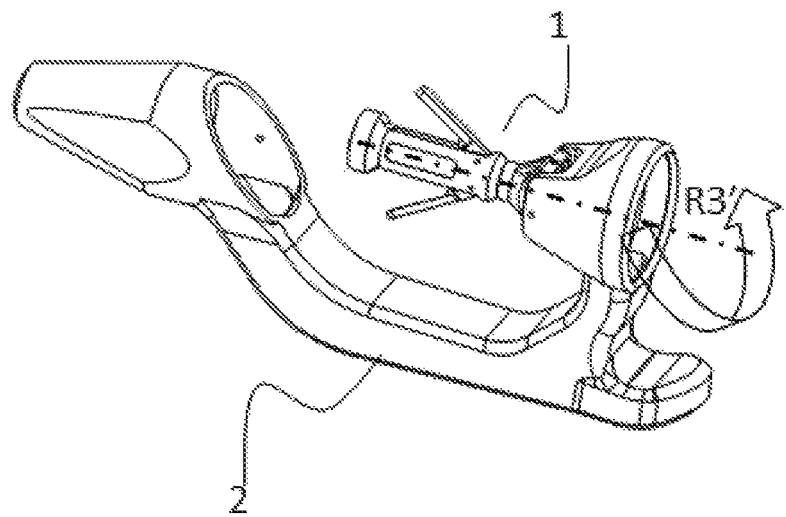
FIG. 21 schematically illustrates an self-rotational degree of freedom of the manipulation component.
Figure 22:
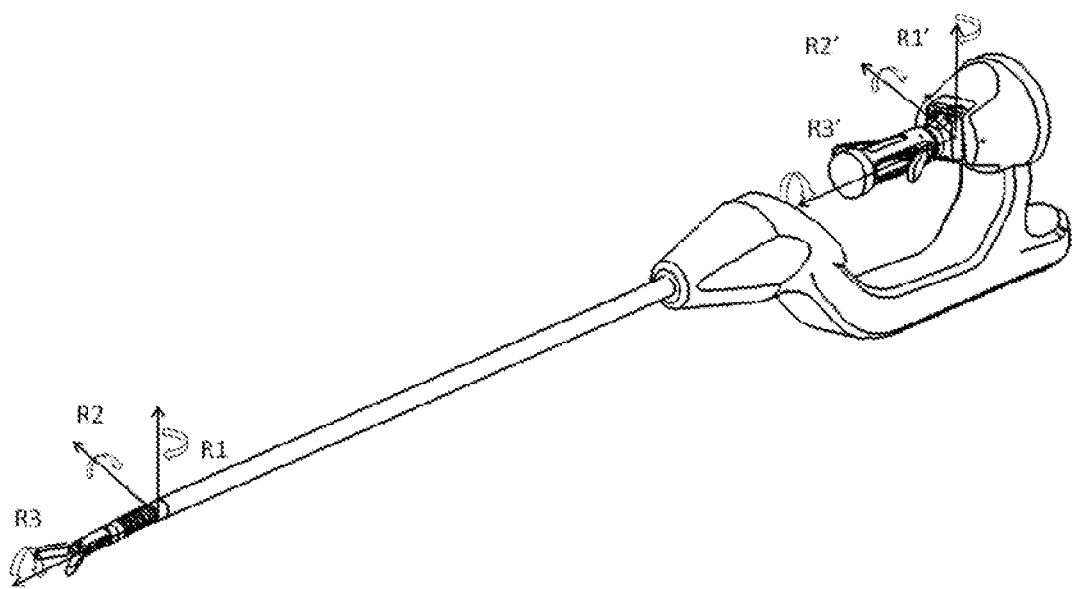
FIG. 22 schematically illustrates all degrees of freedom of the snake-like instrument.

In some embodiments shown in FIG. 21-FIG. 22, the gripping portion 10 and the inner frame 14 of the manipulation component 1 may also be rotatably connected, so that the gripping portion 10 has a rotational freedom R3' about its own axis. Correspondingly, the jaw supporting base 41 of the terminal 4 is rotatable relative to the snake-like component 40, so that the jaw supporting base 41 has a rotational freedom R3 about its own axis. The transmission mechanism further includes a second flexible member. The rotation of the gripping portion 10 drives the second flexible structure to rotate, which in turn drives the jaw supporting base 41 and the end effector in the terminal 4 to rotate. In this way, the terminal 4 is able to realize the autorotation of the end effector through the rotation of the jaw supporting base 41 in the case that the overall structure of the instrument is not rotated, thereby bringing a convenient and fast surgical operation.

The second flexible structure is made of a flexible material that can transmit force, which combines with degrees of freedom of the manipulation component 1 and allows controlling the self-rotation (revolve on its own axis) of the terminal 4, thereby avoiding the inconvenience of rotation of the entire surgical instrument and enhancing the operational stability. Further, the second flexible member may be a nickel titanium wire or the like.

In some embodiments, the first flexible member 52 is made of a flexible material that can transmit torque. The gripping portion 10 drives the first flexible member 52 to self-rotate, thereby driving the jaw supporting base 41 and the end effector in the terminal 4 to rotate. In this way, it is possible to realize the autorotation of the terminal without providing an additional second flexible member.

The features of the above-described embodiments may be combined arbitrarily. While not all possible combinations of these features are described for the sake of brevity, they are all considered within the scope of present disclosure as long as there is no contradiction therein.

The above embodiments describe merely a few embodiments of the present disclosure. While the few embodiments have been described specifically and in detail, they are not intended to be understood as limitations to the scope of the disclosure. It is noted that, many variations and modifications can be made by those of ordinary skill in the art without departing from the spirit of the present disclosure, which fall into the protection scope of the the appended claims.

What is claimed is:

1. A snake-like surgical instrument, comprising:
a hand-held component;
a connecting component;
a manipulation component comprising a hooke joint, wherein the hooke joint comprises an inner frame and an outer frame, wherein the outer frame is hinged with the hand-held component to cause the manipulation component to have a rotational degree of freedom about a first axis, and the inner frame is hinged with the outer frame to cause the manipulation component to have a degree of freedom of rotation about a second axis, the first axis angularly arranged with respect to the second axis;
a terminal connected to the hand-held component via the connecting component, wherein the terminal includes a jaw supporting base, a snake-like component connected to the jaw supporting base, and an end effector mounted on the snake-like component, the snake-like component having two rotational degrees of freedom; and
a transmission mechanism, wherein the transmission mechanism includes a flexible transmission structure for connecting the inner frame and the snake-like component and is configured to cause the manipulation component and the snake structure to rotate in a same direction.

2. The snake-like surgical instrument according to claim 1, wherein the hand-held component includes an arc-shaped body, wherein the arc-shaped body has a proximal end provided with a proximal supporting base, the proximal supporting base having a distal end connected to the manipulation component, and wherein the arc-shaped body has a distal end provided with a distal supporting base, the distal supporting base having a distal end connected to the connecting component.

3. The snake-like surgical instrument according to claim 2, wherein the transmission mechanism further includes a driving wheel mounted on the hand-held component, through which the flexible transmission structure changes direction thereof.

4. The snake-like surgical instrument according to claim 1, wherein the first axis and the second axis are located in a centrosymmetric plane of the outer frame in a thickness direction, and are orthogonal to a center of the centrosymmetric plane.

5. The snake-like surgical instrument according to claim 1, wherein the flexible transmission structure has one end fixed to the inner frame and the other end fixed to the snake-like component, and wherein a position at which the flexible transmission mechanism is fixed to the inner frame and a position at which the flexible transmission mechanism is fixed to the snake-like component are arranged in opposite manners.

6. The snake-like surgical instrument according to claim 1, wherein the manipulation component further comprises a gripping portion connected to the inner frame, and the gripping portion is configured to control movements of the hooke joint.

7. The snake-like surgical instrument according to claim 6, wherein the manipulation component further includes an end effector controller disposed on the gripping portion, and wherein the transmission mechanism further includes a first flexible member, through which the end effector controller controls movements of the end effector.

8. The snake-like surgical instrument according to claim 7, wherein the end effector includes at least one jaw rotatably connected to the jaw supporting base, wherein the end effector controller includes at least one opening/closing segment having one end rotatably connected to the gripping portion, and wherein the opening/closing segment controls a rotation of the at least one jaw via the first flexible member.

9. The snake-like surgical instrument according to claim 8, wherein the end effector includes two jaws that are able to rotate relatively, each of the two jaws rotatably connected to the jaw supporting base, and wherein the opening/closing segment controls a relative rotation of the two jaws via the first flexible member.

10. The snake-like surgical instrument according to claim 9, wherein the transmission mechanism further comprises an elastic structure provided on the gripping portion, the jaw supporting base, or between the two jaws, so as to keep the two jaws normally open.

11. The snake-like surgical instrument according to claim 8, wherein the end effector includes two jaws, one of the two jaws fixedly connected to the jaw supporting base, the other one of the two jaws rotatably connected to the jaw supporting base, and wherein the opening/closing segment controls a relative rotation of the two jaws via the first flexible member.

12. The snake-like surgical instrument according to claim 11, wherein the transmission mechanism further comprises an elastic structure provided on the gripping portion, the jaw supporting base, or between the two jaws, so as to keep the two jaws normally open.

13. The snake-like surgical instrument according to claim 8, wherein the manipulation component further comprises a manipulation end connector connected to the end effector controller, and the terminal further comprises an end effector connector attached to the end effector, wherein the end effector connector includes a first rotating shaft, a second rotating shaft and a first link rod, the first link rod having a proximal end rotatably connected to a distal end of the first flexible member via the first rotating shaft and a distal end connected to a proximal end of the jaw via the second rotating shaft, the first rotating shaft configured to move along an axial direction of the connecting component; wherein the manipulation end connector includes a fourth rotating shaft, a fifth rotating shaft, and a third link rod, the third link rod having a distal end rotatably connected to a proximal end of the first flexible member via the fourth rotating shaft and a proximal end rotatably connected to a distal end of the opening/closing segment, the fourth rotating shaft configured to move along the axial direction of the connecting component.

14. The snake-like surgical instrument according to claim 8, wherein the manipulation component further comprises a manipulation end connector connected to the end effector controller, and the terminal further comprises an end effector connector attached to the end effector, and wherein movements of the end effector controller are transferred to manipulation end connector that transmits the transferred movements to the end effector connector through the first flexible member, which causes the end effector connector to drive the end effector to move.

15. The snake-like surgical instrument according to claim 14, wherein the first flexible member is a soft shaft and the transmission mechanism further includes a compression spring, and wherein the compression spring is disposed between the manipulation end connector and the gripping portion, or between the gripping portion and the opening/closing segment, or in the manipulation end connector, or between the end effector and the jaw supporting base, or in the end effector.

16. The snake-like surgical instrument according to claim 14, wherein the end effector includes a left jaw and a right jaw, and the first flexible member includes a flexible elongated body, and wherein the transmission mechanism further includes a compression spring disposed between the left jaw and the right jaw.

17. The snake-like surgical instrument according to claim 14, wherein one end of the first flexible member is connected to the end effector connector and the other end of the first flexible member is connected to the manipulation end connector by passing through the gripping portion; or wherein the hand-held component is provided with a driving wheel, and wherein one end of the first flexible member is connected to the end effector connector and the other end of the first flexible member is connected to the manipulation end connector by changing an extending direction thereof via the driving wheel mounted on the hand-held component.

18. The snake-like surgical instrument according to claim 8, wherein the opening/closing segment is provided with a finger cuff.

19. The snake-like surgical instrument according to claim 6, wherein the gripping portion is rotatably connected to the inner frame to cause the gripping portion have a rotational degree of freedom about an axis of the gripping portion and cause the jaw supporting base has a rotational degree of freedom about an axis of the jaw supporting base with respect to the snake-like component, and wherein the transmission mechanism further comprises a second flexible structure, through which the gripping portion transmit rotation movements to the jaw supporting base, so as to drive the end effector to rotate around the axis of the jaw supporting base.

* * * * *